United States Patent [19]
Souza et al.

[11] Patent Number: 5,353,795
[45] Date of Patent: Oct. 11, 1994

[54] TRACKING SYSTEM TO MONITOR THE POSITION OF A DEVICE USING MULTIPLEXED MAGNETIC RESONANCE DETECTION

[75] Inventors: Steven P. Souza, Williamstown, Mass.; Charles L. Dumoulin, Ballston Lake; Robert D. Darrow, Scotia, both of N.Y.

[73] Assignee: General Electric Company, Schenectady, N.Y.

[21] Appl. No.: 989,283

[22] Filed: Dec. 10, 1992

[51] Int. Cl.⁵ .............................................. A61B 5/055
[52] U.S. Cl. ........................... 128/653.2; 128/653.5; 128/658
[58] Field of Search ................... 128/653.2, 653.5, 899, 128/658

[56] References Cited

U.S. PATENT DOCUMENTS

| | | | |
|---|---|---|---|
| 4,254,778 | 3/1981 | Clow et al. | 128/653.2 |
| 4,527,198 | 2/1986 | Codrington | 128/653.2 |
| 4,613,837 | 9/1986 | Blass et al. | 128/653.5 |
| 4,638,252 | 1/1987 | Bradshaw | 128/653.5 |
| 4,672,972 | 6/1987 | Berke | 128/653.5 |
| 4,799,015 | 1/1989 | Sepponen | 128/653.2 |
| 4,889,127 | 12/1989 | Takeda et al. | 128/653.2 |
| 4,962,763 | 10/1990 | Sato et al. | 128/653.2 |
| 4,966,149 | 10/1990 | Stokar | 128/653.2 |
| 4,989,608 | 2/1991 | Ratner | 128/653.2 |
| 4,995,394 | 2/1991 | Cline et al. | 128/653.2 |
| 5,005,592 | 4/1991 | Cartmell | 128/899 |
| 5,042,486 | 8/1991 | Pfeiler et al. | 128/653.1 |
| 5,099,895 | 3/1992 | Besz et al. | 128/899 |
| 5,107,862 | 4/1992 | Fabian et al. | 128/899 |
| 5,170,789 | 12/1992 | Narayan et al. | 128/653.5 |

FOREIGN PATENT DOCUMENTS

| | | |
|---|---|---|
| 0385367 | 9/1990 | European Pat. Off. . |
| 3937052 | 5/1990 | Fed. Rep. of Germany . |

*Primary Examiner*—Lee S. Cohen
*Assistant Examiner*—Brian L. Casler
*Attorney, Agent, or Firm*—Lawrence P. Zale; Marvin Snyder

[57] ABSTRACT

A tracking system employs magnetic resonance signals to monitor the position of a device such as a catheter within a subject. The device has a receiver coil which is sensitive to magnetic resonance signals generated in the subject. These signals are detected in the presence of magnetic field gradients and thus have frequencies which are substantially proportional to the location of the coil along the direction of the applied gradient. Signals are detected responsive to applied magnetic gradients to determine the position of the device in several dimensions. Sensitivity of the measured position to resonance offset conditions such as transmitter frequency misadjustment, chemical shift and the like is minimized by repeating the process a plurality of times with selected amplitudes and polarities for the applied magnetic field gradient. Linear combinations of the data acquired responsive to the different applied magnetic field gradients are computed to determine the position of the device in three orthogonal dimensions. The position of the device as determined by the tracking system is superimposed upon independently acquired medical diagnostic images.

17 Claims, 8 Drawing Sheets

TRACKING SYSTEM TO MONITOR THE POSITION OF A DEVICE USING MULTIPLEXED MAGNETIC RESONANCE DETECTION

CROSS REFERENCES TO RELATED APPLICATIONS

This application is related to U.S. patent applications TRACKING SYSTEM AND PULSE SEQUENCES TO MONITOR THE POSITION OF A DEVICE USING MAGNETIC RESONANCE, Ser. No. 07/861,718, TRACKING SYSTEM TO MONITOR THE POSITION AND ORIENTATION OF A DEVICE USING MAGNETIC RESONANCE DETECTION OF A SAMPLE CONTAINED WITHIN THE DEVICE, Ser. No. 07/861,662 and TRACKING SYSTEM TO MONITOR THE POSITION AND ORIENTATION OF A DEVICE USING MULTIPLEXED MAGNETIC RESONANCE DETECTION, Ser. No. 07/861,690 by Dr. Charles L. Dumoulin, Dr. Steven P. Souza and Robert D. Darrow all assigned to the present assignee, hereby incorporated by reference, and filed on Apr. 1, 1992.

1. Field of the Invention

The present invention relates to medical procedures in which a device is inserted into a body, and more particularly concerns tracking of such device with the use of magnetic resonance signals.

2. Description of Related Art

Several methods of using radiofrequency (RE) signals to track a device in the body have been disclosed in U.S. patent applications TRACKING SYSTEM TO FOLLOW THE POSITION AND ORIENTATION OF A DEVICE WITH RADIOFREQUENCY FIELD GRADIENTS Ser. No. 07/753,565 by C. Dumoulin, R. Darrow, J. Schenck and S. Souza; TRACKING SYSTEM TO FOLLOW THE POSITION AND ORIENTATION OF A DEVICE WITH RADIOFREQUENCY FIELDS Ser. No. 07/753,563 by C. Dumoulin, R. Darrow, J. Schenck and P. Roemer; STEREOSCOPIC X-RAY FLUOROSCOPY SYSTEM USING RADIOFREQUENCY FIELDS Ser. No. 07/753,564 by C. Dumoulin and R. Darrow; AUTOMATIC GANTRY POSITIONING FOR IMAGING SYSTEMS Ser. No. 07/753,567 by R. Darrow and C. Dumoulin; and MULTI-PLANAR X-RAY FLUOROSCOPY SYSTEM USING RADIOFREQUENCY FIELDS Ser. No. 07/753,566 by R. Darrow and C. Dumoulin all filed on Sep. 3, 1991. These methods employ an RF transmitting and receiving apparatus to track a coil attached to the device in a living body.

Magnetic resonance signals have been employed to determine the location of a device in the body disclosed by the above-referenced U.S. patent applications Ser. Nos. 07/861,718; 07/861,662 and 07/861,690. Position information is obtained in three orthogonal directions by successively measuring data in each of three orthogonal dimensions. Data from each dimension is obtained twice, once for each polarity of an applied magnetic field gradient, to correct for artifacts arising from resonance offset conditions such as transmitter misadjustments and susceptibility effects. These disclosed techniques therefore require six measurements to locate the device in three dimensions.

Currently there is a need for a system which tracks a device within a subject in a magnetic resonance (MR) imaging system at a near real-time rate without requiring substantial additional equipment.

SUMMARY OF THE INVENTION

Tracking of catheters and other devices being positioned within a living body, is accomplished by using a magnetic resonance (MR) imaging system comprised of a magnet, pulsed magnetic field gradient system, a radiofrequency transmitter, a radiofrequency receiver and a controller. A device to be tracked is modified by attaching to it a small radiofrequency (RF) coil near its end. A subject is placed in the magnet bore and the device is introduced into the subject. The MR system generates a series of RF and magnetic field gradient pulses transmitted into the subject which induce a resonant MR response signal from selected nuclear spins within the subject. This response signal induces current in the RF coil attached to the device. Since the RF coil is small, its region of sensitivity is limit. Consequently, only nuclear spins in the immediate vicinity of the RF coil are detected by the RF coil. A receiver system receives the detected MR response signal and demodulates, amplifies, filters and digitizes the MR response signal, which is then stored as data by a controller.

Data is acquired during the application of magnetic field gradients in three mutually orthogonal directions. These gradients cause the frequency of the detected signal to be directly proportional to the position of the RF coil along each applied gradient. Subsequent acquisition of data is performed responsive to different combinations of magnetic field gradient pulse polarity and intensity. Linear combinations of the acquired data are then computed to extract position information along three mutually orthogonal axes. The digitized data are then processed using Fourier transformations to calculate the position of the RF coil in three dimensions. This position information can be superimposed on an medical diagnostic image of the region of interest from an imaging means.

OBJECTS OF THE INVENTION

It is an object of the present invention to provide a method of tracking a device in a living body during a magnetic resonance (MR) examination.

It is another object of the present invention to provide an interactive display of the location of a device superimposed upon a medical image.

It is another object of the present invention to provide a method of tracking a device in a living body using multiplexed detection of MR signals.

BRIEF DESCRIPTION OF THE DRAWINGS

The features of the invention believed to be novel are set forth with particularity in the appended claims. The invention itself, however, beth as to organization and method of operation, together with further objects and advantages thereof, may be best understood by reference to the following description taken in conjunction with the accompanying drawings in which:

DETAILED DESCRIPTION OF THE INVENTION

Figure 1:
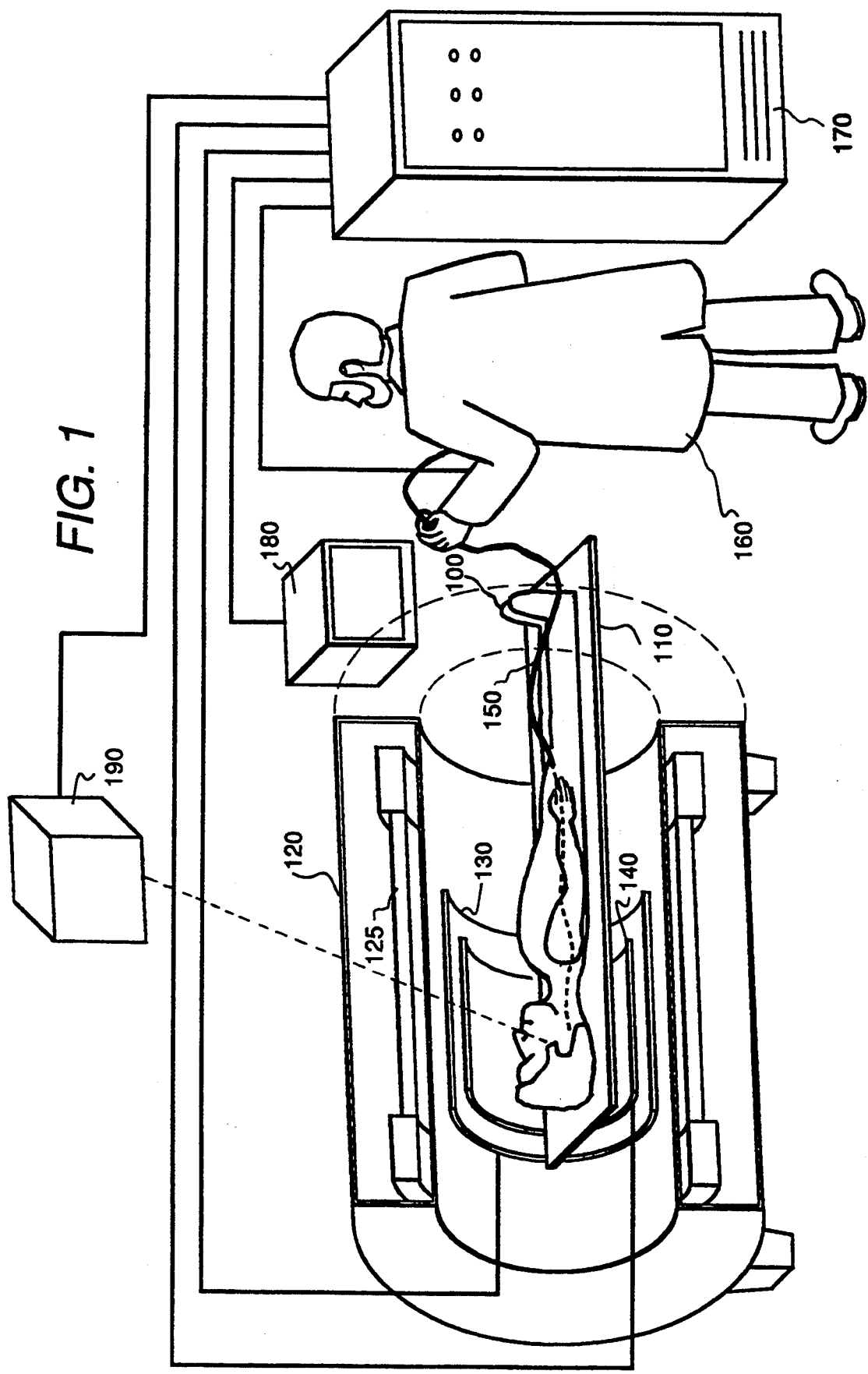
FIG. 1 is a perspective, partially cut-away view of an embodiment of the present invention in operation tracking the location of a device in a subject.

In FIG. 1, a subject 100 on a support table 110 is placed in a homogeneous magnetic field generated by a magnet 125 in magnet housing 120. Magnet 125 and magnet housing 120 have cylindrical symmetry and are shown sectioned in half to reveal the position of subject 100. A region of subject 100 into which a device 150, shown as a catheter, is inserted, is located in the approximate center of the bore of magnet 125. Subject 100 is surrounded by a set of cylindrical magnetic field gradient coils 130 (shown sectioned in half) which create magnetic field gradients of predetermined strength at predetermined times. Gradient coils 130 generate magnetic field gradients in three mutually orthogonal directions.

An external coil 140 also surrounds a region of interest of subject 100. Coil 140 is shown (sectioned in half) as a cylindrical external coil which has a diameter sufficient to encompass the entire subject. Other geometries, such as smaller cylinders specifically designed for imaging the head or an extremity can be used instead. Non-cylindrical external coils, such as surface coils, may alternatively be used. External coil 140 radiates radiofrequency energy into subject 100 at predetermined times and at a predetermined frequency so as to nutate nuclear magnetic spins of atomic nuclei of subject 100 in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Device 150 is inserted into subject 100 by an operator 160, and may be a guide wire, a catheter, an endoscope, a laparescope, a biopsy needle or similar device. This device contains an RF coil which detects MR signals generated in the subject responsive to the radiofrequency field created by external coil 140. Since the RF coil is small, the region of sensitivity is also small. Consequently, the detected signals have Larmor frequencies which arise only from the strength of the magnetic field in the immediate vicinity of the coil. These detected signals are sent to an imaging and tracking unit 170 where they are analyzed. The position of device 150 is determined in imaging and tracking unit 170 and is displayed on a display means 180. In the preferred embodiment of the invention the position of device 150 is displayed on display means 180 by superposition of a graphic symbol on a conventional MR image driven by a superposition means within imaging and tracking unit 170. In alternative embodiments of the invention, the graphic symbol representing device 150 is superimposed on diagnostic images obtained from an imaging means 190 which may be an X-ray, a computed tomography (CT), a Positron Emission Tomography or ultrasound imaging device. Other embodiments of the invention display the position of the device numerically or as a graphic symbol without reference to a diagnostic image.

Figure 2:
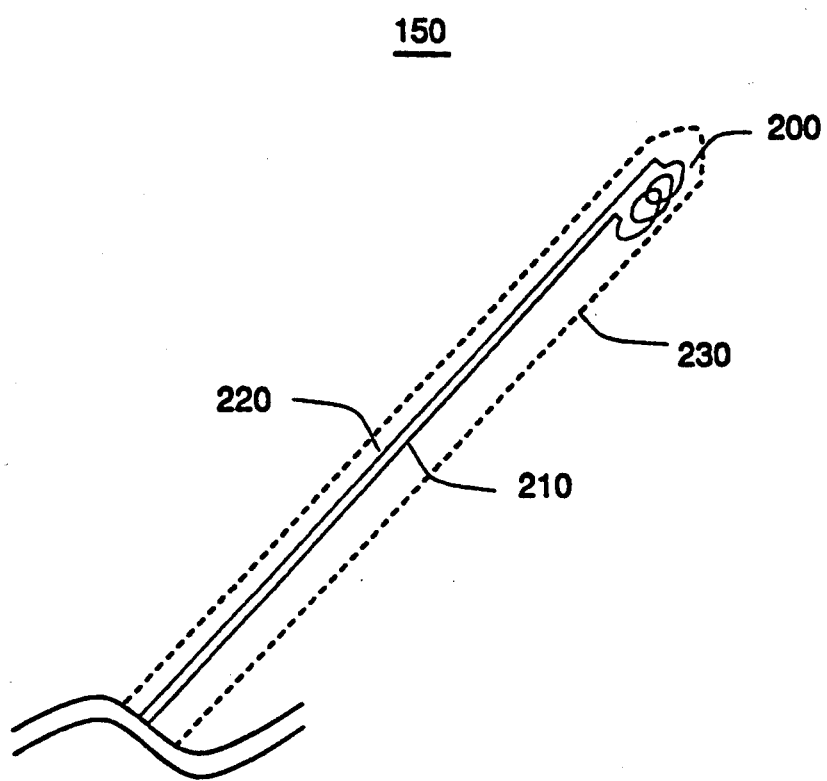
FIG. 2 is a schematic illustration showing an RF coil incorporated into a device intended to be inserted into the body of a subject.

An embodiment of device 150 is shown in greater detail in FIG. 2. A small RF coil 200 is electrically coupled to the MR system via conductors 210 and 220. In the preferred embodiment of this invention, conductors 210 and 220 form a co-axial pair. Conductors 210 and 220 and RF coil 200 are encased in a outer shell 230 of device 150. The MR signal arising from the tissue surrounding device 150 is detected by coil 200.

Figure 3:
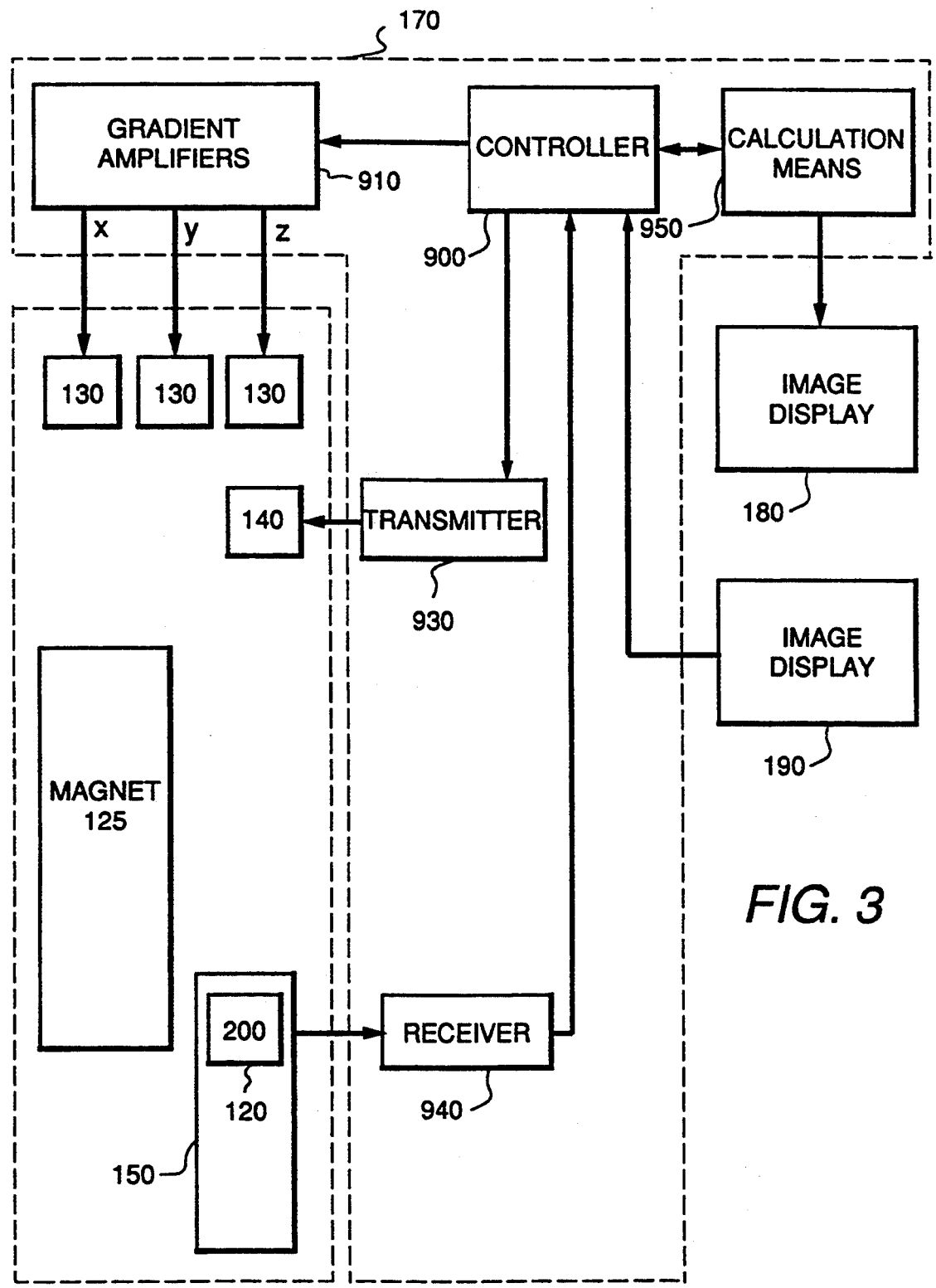
FIG. 3 is a block diagram of an MR imaging system suitable for tracking the device of FIG. 2 according to the present invention.

FIG. 3 is a block diagram of an MR system suitable for imaging and device tracking. The system comprises a controller 900 which provides control signals to a set of magnetic field gradient amplifiers 910. These amplifiers drive magnetic field gradient coils 130 situated within the magnet enclosure 120 (also shown in FIG. 1). Gradient coils 130 are capable of generating magnetic field gradients in three mutually orthogonal directions. Controller 900 also generates signals which are sent to a transmitter means 930. These signals may correspond to a "zero reference" magnetic resonance tracking sequence or a "Hadamard" magnetic resonance tracking sequence. The signals from controller 900 cause transmitter means 930 to generate RF pulses at a selected frequency and of suitable power to nutate selected spins in the region of the subject situated within external coil 140 which, in turn, is situated within the bore of magnet 125. An MR signal is induced in RF coil 200, (also shown in FIG. 2) connected to a receiver means 940. Receiver means 940 processes the MR signal by amplifying, demodulating, filtering and digitizing it. Controller 900 also collects signals from receiver means 940 and propagates it to a calculation means 950 where it is processed. Calculation means 950 applies a Fourier transformation to the signal received from controller 900 to arrive at a location of coil 200. Images of the subject are provided to controller 900 by imaging means 190. These images may be generated by an ultrasound, X-ray, positron emission tomography, or computed temography imaging device. A symbol is positioned on the image at a position corresponding to the location of coil 200 calculated by calculation means 950 on an image display means 180.

Figure 4:
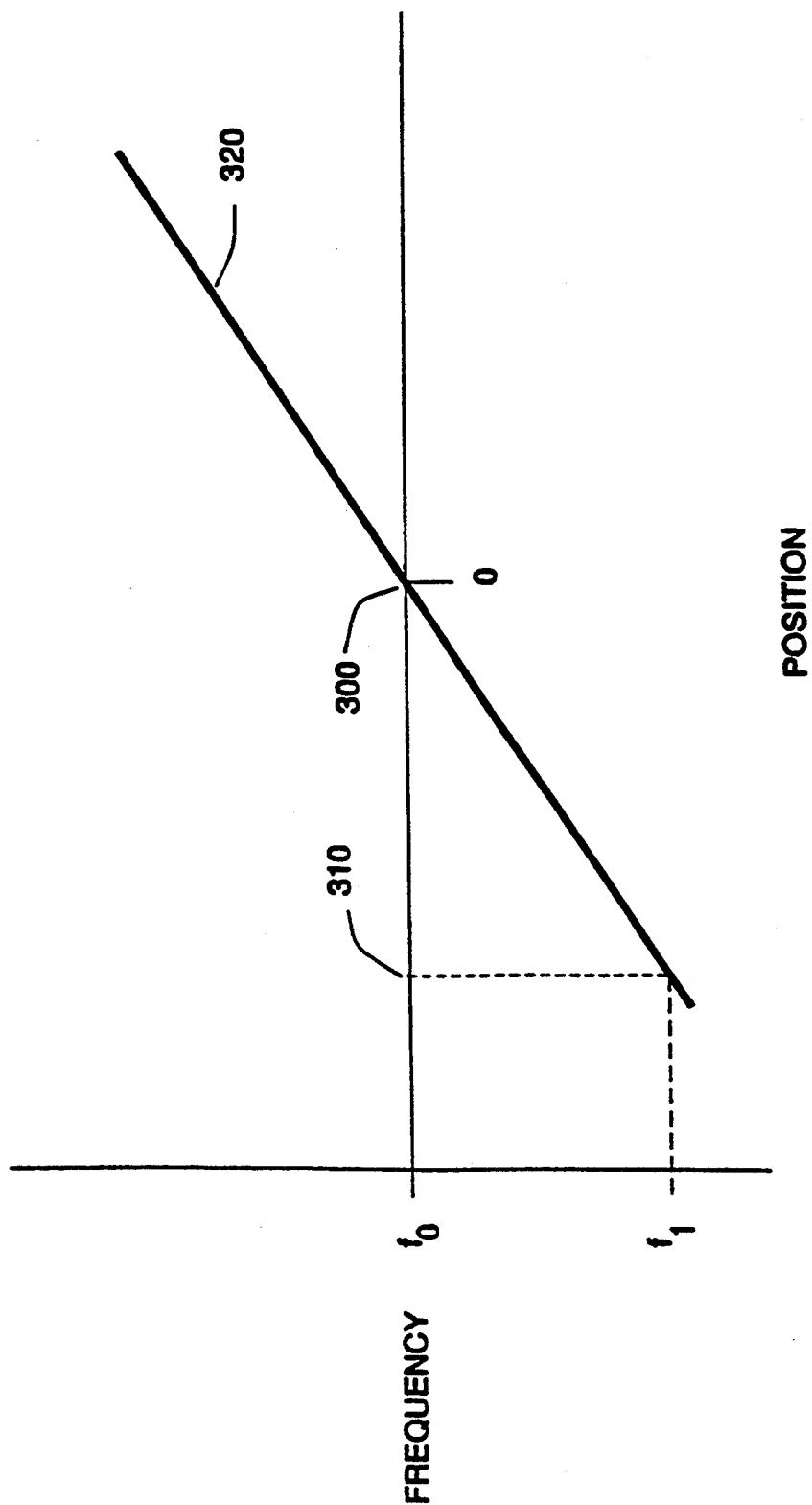
FIG. 4 is a graph of MR resonance frequency vs. position along a single axis in the presence of an applied magnetic field gradient.

Referring now to FIG. 4, the Larmor frequency of a spin is shown to be substantially proportional to its position when a magnetic field gradient is applied. A spin located at a center point 300 of gradient coil 130 (FIG. 1) precesses at a Larmor frequency $f_0$. The Larmor frequency $f_0$ at point 300 is determined solely by the static magnetic field generated by magnet 125 (FIG. 1). A spin at a location 310 has a Larmor frequency $f_1$ determined by the sum of the static magnetic field and the additional magnetic field created at that location by magnetic field gradient coil 130 (FIG. 1). Since the gradient coil response 320 is substantially linear, the Larmor frequency of the spin is substantially proportional to position.

Figure 5A:
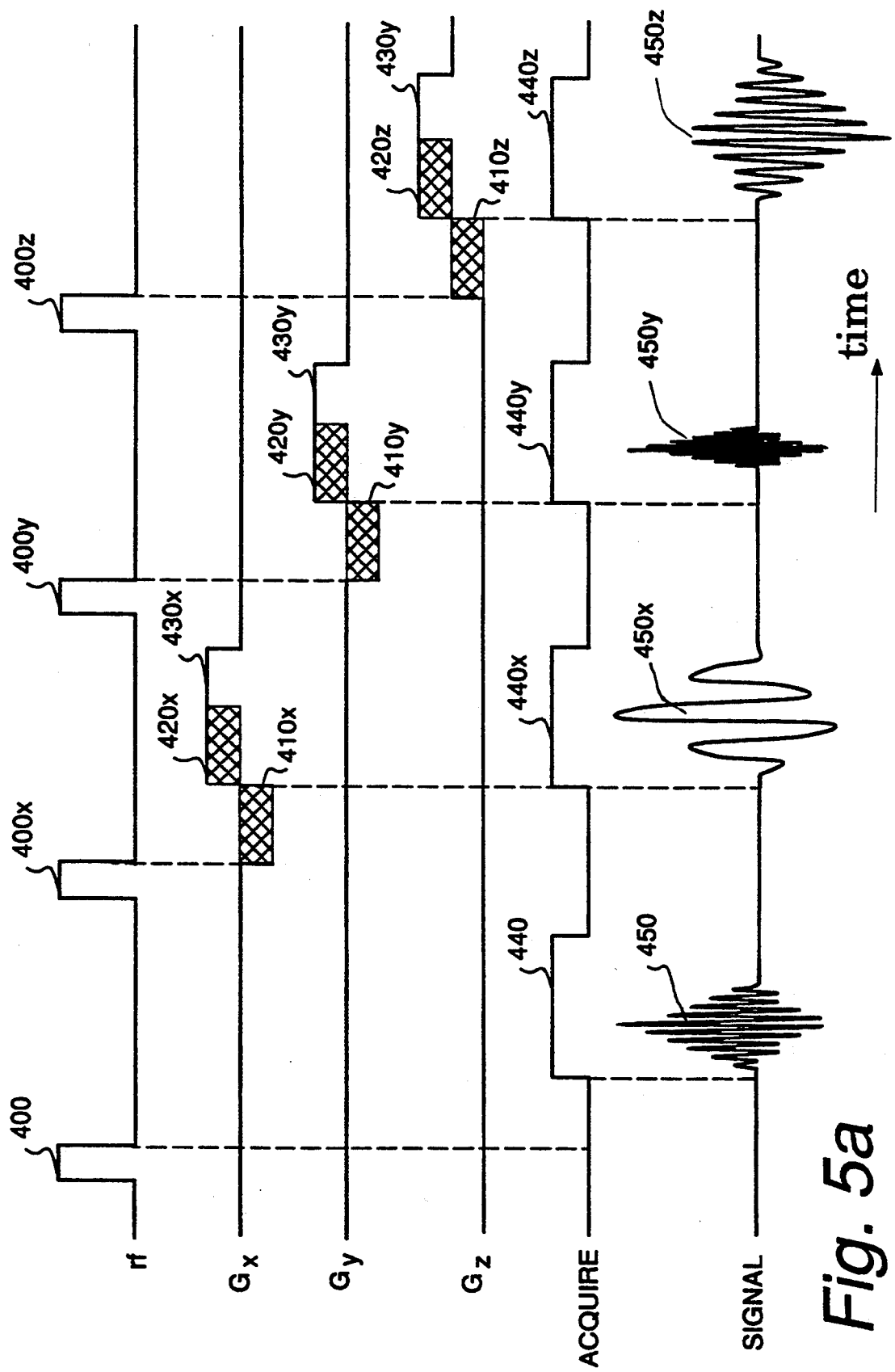
FIG. 5a is a diagram of a "zero reference MR tracking sequence" of the present invention showing the relationships between RF pulses, magnetic field gradient pulses, data acquisition and detected signals.

The MR response signal detected by RF coil 200 encased in device 150 as shown in FIG. 2 is generated in response to the RF and magnetic field gradient pulses of the MR system. A presently preferred embodiment of the pulse timing is illustrated in FIG. 5a, which shall be referred to as the "zero reference magnetic resonance tracking sequence". In this timing diagram, a zero reference broadband RF pulse 400 is applied. A data acquire signal 440 is then generated to cause a zero reference MR response signal 450 to be digitized and stored in imaging and tracking unit 170 of FIG. 1. Zero reference MR response signal 450 is detected in the absence of magnetic field gradients. Consequently, the position given by the frequency of zero reference MR response signal 450 is the detected center of the imaging system. If, however, resonance offset conditions such as transmitter frequency misadjustment, susceptibility effects and the like exist, the detected position will differ from the actual center of the imaging system by an amount proportional to the size of the resonance offset. The measured error due to resonance offset will be subtracted from each of three orthogonal positions computed responsive to a tint, second and third data acquire signals 440x, 440y and 440z.

First broadband RF pulse 400x excites all spins of the subject within external coil 140 of FIG. 1. After first broadband RF pulse 400x, a tint magnetic field gradient pulse 410x is applied in a predetermined direction. Gradient pulse 410x dephases spin magnetization to a degree proportional to the position of the spin along the applied field gradient (shown here to be in the X direction). Gradient pulse 410x is followed by a second magnetic field gradient pulse 420x having an opposite polarity to form a bi-lobed magnetic field gradient pulse. The product of the magnetic field gradient magnitude and duration of the gradient pulses (i.e., the cross-hatched regions) is chosen to be substantially identical for the first and second gradient pulses. The amplitude of second magnetic field gradient pulse 420x is then maintained for a duration substantially equal to that of second magnetic field gradient pulse 420x, effectively creating a third pulse 430x having an area substantially identical to that of second pulse 420x. Second and third gradient pulses 420x and 430 x, respectively, in fact form a single pulse, which has been divided into two pulses solely for purposes of identification. At the end of the second gradient pulse, all spins in the subject are substantially in phase. Third gradient pulse 430x causes additional dephasing of the MR signal.

During second gradient pulse 420x and third gradient pulse 430x, a data acquire signal 440x causes a first MR response signal 450x to be received by RF coil 200 (FIG. 2). MR response signal 450x is digitized and stored in imaging and tracking unit 170 (FIG. 1). MR response signal 450x reaches a maximum amplitude substantially at the end of second gradient pulse 420x and exhibits a Larmor frequency which is substantially proportional to the position of device 150 (FIG. 1 ) along the direction of the applied magnetic field gradient. The frequency of MR response signal 450x is used to determine the position of device 150 (FIG. 1) in a first direction which is parallel to the direction of the applied field gradient, $G_x$.

A second broadband RF pulse 400y is applied immediately after acquisition of first MR response signal 450x. In a manner analogous to that used to determine the position of device 150 of FIG. 1 in the first direction, fourth, fifth and sixth gradient pulses 410y, 420y, 430y, respectively, are applied in a second direction (here indicated to be in the Y direction) substantially orthogonal to the first direction. A data acquire signal 440y is generated during the period of the fifth and sixth gradient pulses 420y, 430y to cause a second MR response signal 450y to be digitized and stored in imaging and tracking unit 170 of FIG. 1. The frequency of MR response signal 450y is used to determine the position of device 150 (of FIG. 1) in second direction Y. After detection of MR response signal 450y, a third broadband RF pulse 400z is applied and seventh, eighth and ninth gradient pulses 410z, 420z, 430z, respectively, are applied in a third direction (shown here to be in the Z direction) substantially orthogonal to the first and second directions. A data acquire signal 440z is generated during the period of the eighth and ninth gradient pulses to cause a third MR response signal 450z to be digitized and stored in imaging and tracking unit 170 of FIG. 1. The frequency of MR response signal 450z is used to determine the position of device 150 (of FIG. 1) in third direction Z.

After detection of third MR response signal 450z the measured error due to resonance offset obtained from zero reference MR response signal 450 is subtracted in imaging and tracking unit 170 from each of the X, Y, and Z positions, to determine the actual location of the device which is then displayed on display means 180. The entire pulse sequence shown in FIG. 5a is then repeated until tracking of the device is no longer desired. Alternatively, the entire pulse sequence shown in FIG. 5a is periodically interleaved with an imaging pulse sequence acquiring MR response signals from a conventional imaging RF coil to effect substantially simultaneous imaging of the subject and tracking of the device.

In another embodiment of this invention, the durations of third, sixth and ninth gradient pulses 430x, 430y, 430z, respectively, are extended to ensure that the signals are completely dephased before application of the next broadband RF pulse. This minimizes artifacts arising from spin phase coherence from multiple RF pulses. A second method of minimizing phase coherence is to use random phases in the MR system RF receiver and transmitter for each RF pulse.

In still another embodiment of this invention, the first, fourth and seventh gradient pulses 410x, 410y, 410z, respectively, are reduced in amplitude and/or duration without changing the remaining gradient pulses. This reduces the amount of dephasing each signal experiences prior to the data acquisition period and thus shifts the instant of maximum signal, but not its frequency. Reducing the duration of the first, fourth and seventh gradient pulses 410x, 410y, 410z, respectively, permits an advantageous reduction in the RF pulse interval.

Figure 5B:
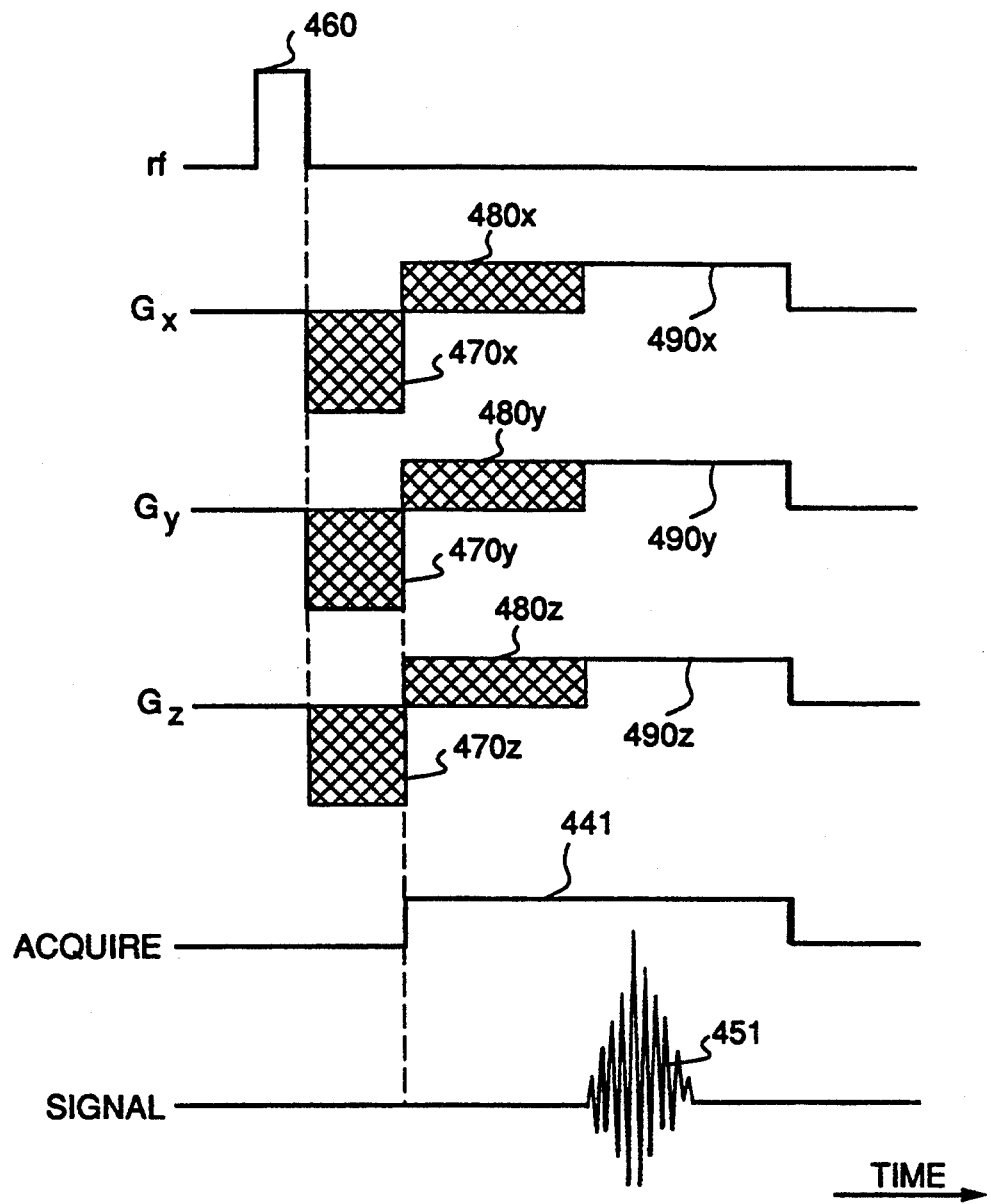
FIG. 5b is a diagram of a "Hadamard MR tracking sequence" of the present invention showing the relationships between RF pulses, magnetic field gradient pulses, data acquisition and detected signals.

The pulse sequence shown in FIG. 5a can be modified to become the "Hadamard magnetic resonance tracking sequence" shown in FIG. 5b. In this embodiment of the invention a broadband RF pulse 460 is used. Three dephasing magnetic field gradient pulses 470x, 470y, 470z are applied substantially simultaneously to dephase spins along the three mutually orthogonal axes. Readout magnetic field gradient pulses 480x, 480y, 480z are simultaneously applied after the dephasing gradient pulses. A data acquire signal 441 is applied as in the pulse sequence of FIG. 5a to cause a response signal 451 to be collected by the MR system. It will be noted that each set of readout dephasing and readout gradient pulses forms a bi-lobed gradient pulse.

After the detection of response signal 451 the pulse sequence shown in FIG. 5b is repeated with different polarity magnetic field gradient pulses 470x, 470y, 470z, 480x, 480y, 480z, 490x, 490y, 490z. In one preferred embodiment of the invention, the polarities of the magnetic field gradient pulses are chosen according to a Hadamard encoding matrix. One example of a Hadamard encoding matrix for a number of excitations being four excitation, is:

|  | Gradient Pulses | | |
| --- | --- | --- | --- |
|  | X | Y | Z |
| Excitation 1 | − | − | − |
| 2 | + | + | − |
| 3 | + | − | + |
| 4 | − | + | + |

Here "+" denotes a magnetic field gradient pulse applied in a selected direction and "−" denotes a substantially identical gradient pulse applied along the same axis, but of opposite polarity.

In the Hadamard encoding embodiment of the invention shown in FIG. 5b, four of response signals 451 are stored in imaging and tracking unit 170 of FIG. 1. A position from each of the four response signals P1, P2, P3, P4 is calculated by computing the Fourier transformation of the response signals in a fashion similar to that described for the pulse sequence shown in FIG. 5a, and in FIG. 6 below. Linear combinations of the four positions P1, P2, P3, P4 are then computed to obtain three processed response signals which are sensitive to the position of the device with respect to the X, Y and Z magnetic field gradient axes respectively. For the Hadamard encoding embodiment in which NEX=4 the following linear combinations are useful:

X position = P1 − P2 − P3 + P4

Y position = P1 − P2 + P3 − P4

Z position = P1 + P2 − P3 − P4

It is important to note that the position of device 150 of FIG. 1 obtained with the "zero reference MR tracking sequence" outlined in FIG. 5a or with the "Hadamard MR tracking sequence" outlined in FIG. 5b is insensitive to differences in chemical shift which might occur as the device passes different types of tissue or other resonance offset conditions such as transmitter frequency misadjustment.

Figure 6:
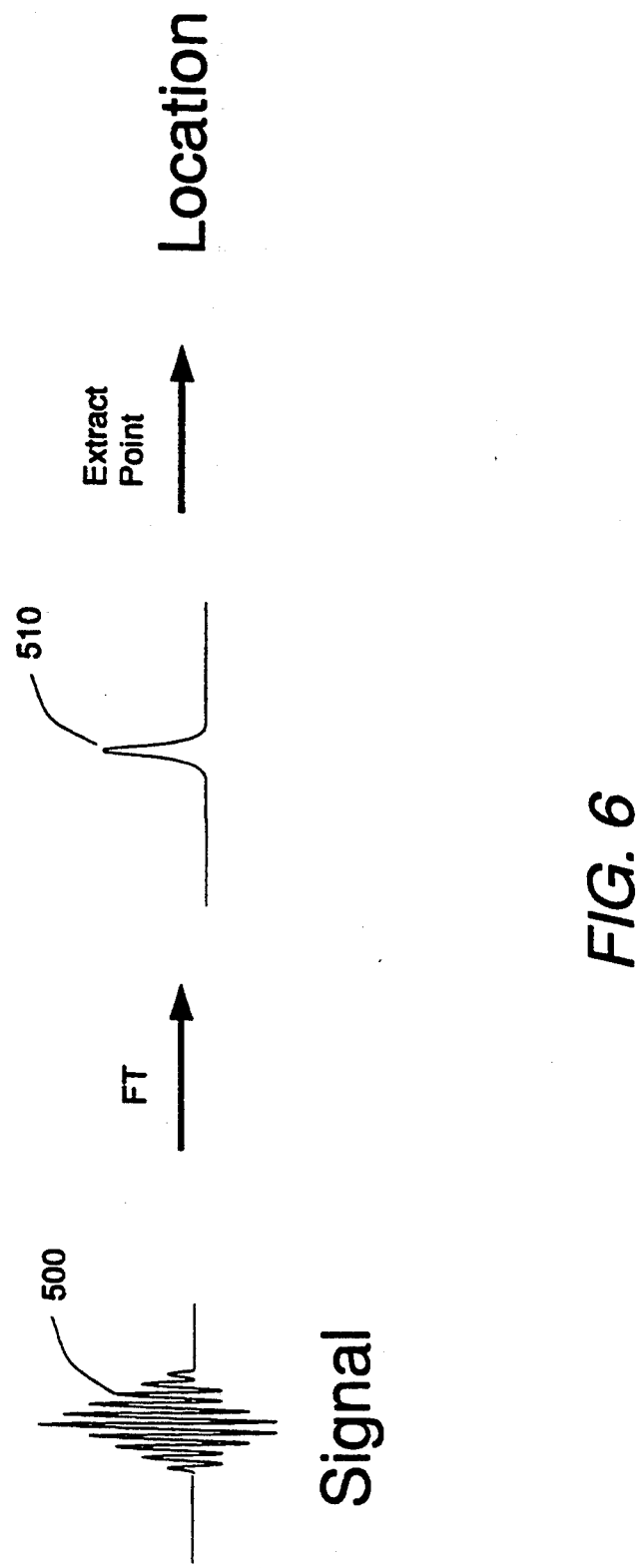
FIG. 6 is a diagram illustrating the steps required to determine the location of an RF coil along the direction of an applied magnetic field gradient.

Referring now to FIG. 6, the stops executed by imaging and tracking unit 170 of FIG. 1 to determine the position of device 150 of FIG. 1 from the detected signals are illustrated. A signal 500, is detected by the MR system responsive to the pulse sequence shown in either FIG. 5a or FIG. 5b. Signal 500 contains information about the position of the device in the direction of the applied magnetic field gradient. This frequency information is extracted by subjecting the signal to a Fourier transformation (FT) which converts the time dependency of the data to frequency dependency. The frequency dependent data set 510 contains a single maximum which corresponds to a position of RF coil 200 of FIG. 2 in the direction of the applied field gradient. The location of the maximum value in the data set is extracted and passed to the display means 180 (FIG. 1) for presentation to the operator.

MR imaging and device tracking can be performed with much of the same hardware system if desired. It is also possible to interleave image acquisition with tracking so that both are performed approximately at the same time. Alternatively, simultaneous tracking and imaging can be done without interleaving by analyzing the gradient waveforms of an imaging procedure and the MR response signal detected by RF coil 200 within device 150 (of FIG. 2) to determine the location of device 150.

In a preferred embodiment of the invention, RF coil 200 located within device 150 performs a receive function. Reciprocity between the transmit and receive coils exists, however, and tracking systems in which RF coil 200 in device 150 is used to transmit RF energy, and external coil 140 is used to receive the MR response signal are possible.

Figure 7:
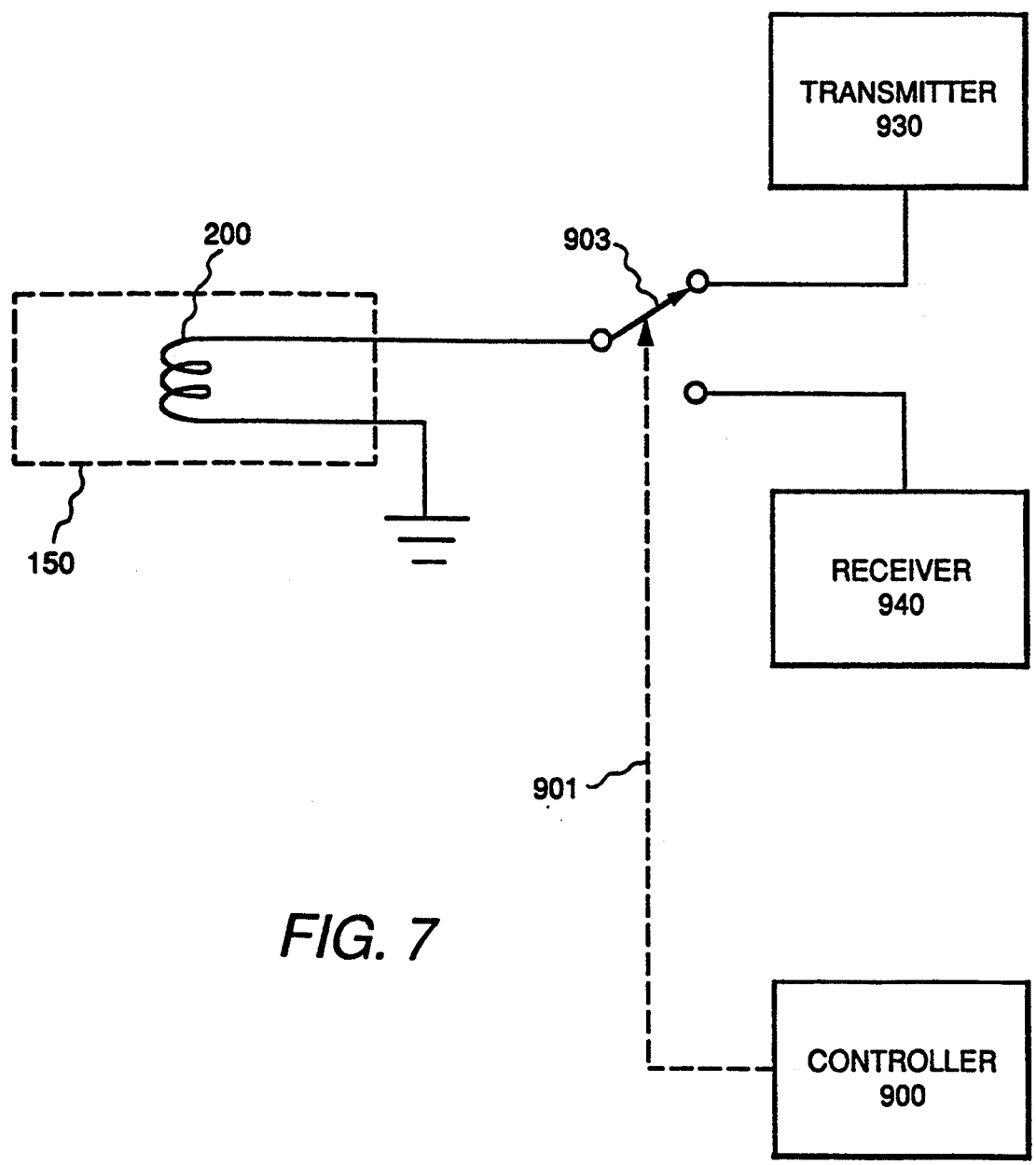
FIG. 7 is a partial block diagram of another embodiment of an MR tracking system according to the present invention.

In another embodiment of the invention, RF coil 200 may be used to alternately transmit and receive RF energy as shown in FIG. 7. A controller 900 activates a switch 903 in accordance with the MR sequence being used to connect coil 200 to transmitter 930 for transmitting RF energy into the subject. Conversely, controller 900 activates switch 903 to connect coil 200 to receiver 940 for receiving RF energy from the subject.

While several presently preferred embodiments of the novel MR tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance tracking system for monitoring a location of a device within a subject, comprising:
   a) a device adapted to be inserted within said subject;
   b) magnetic field means adapted for applying a homogeneous magnetic field having substantially uniform amplitude over said subject;
   c) radiofrequency (RF) transmitter means adapted for transmitting RF energy of a selected duration, amplitude and frequency into said subject to cause nutation of a selected ensemble of nuclear spins in said subject;
   d) gradient means adapted for varying the amplitude of the magnetic field in a selected number of spatial dimensions to form a magnetic field gradient in a selected direction;
   e) detection means attached to the device adapted for detecting a magnetic resonance (MR) response signal from the selected ensemble of spins;
   f) calculation means responsive to the detection means adapted for calculating a location of said device from the detected MR response signals;
   g) controller means coupled to the transmitter means, the detection means, the calculation means and the means for varying the magnetic field, said controller means being adapted for activating the transmitter means, the detection means, the calculation means and the means for varying the magnetic field according to a zero reference magnetic resonance tracking sequence; and
   h) display means responsive to the calculation means adapted for displaying the location of said device to an operator.

2. The magnetic resonance tracking system recited in claim 1 further comprising:
   a) imaging means for acquiring a medical diagnostic image of said subject; and
   b) superposition means for superimposing a symbol on the medical diagnostic image at a position representing the calculated location of said device.

3. The magnetic resonance tracking system recited in claim 2, wherein the imaging means comprises one of the group consisting of a: magnetic resonance, X-ray, computed tomography (CT), positron emission tomography and ultrasound imaging system.

4. A magnetic resonance tracking system for monitoring a location of a device within a subject, comprising:
   a) a device adapted to be inserted within said subject;
   b) magnetic field means adapted for applying a homogeneous magnetic field having substantially uniform amplitude over said subject;
   c) radiofrequency (RF) transmitter means attached to the device adapted for transmitting RF energy of a selected duration, amplitude and frequency into said subject to cause nutation of a selected ensemble of nuclear spins in said subject;
   d) gradient means adapted for varying the amplitude of the magnetic field in a selected number of dimensions over time;
   e) detection means adapted for detecting a magnetic resonance (MR) response signal from the selected ensemble of spins;
   f) calculation means responsive to the detection means adapted for calculating a location of said device from the detected MR response signal;
   g) controller means coupled to the transmitter means, the detection means, the calculation means and the means for varying the magnetic field, said controller means being adapted for activating the transmitter means, the detection means, the calculation means and the means for varying the magnetic field according to a Hadamard magnetic resonance tracking sequence; and
   h) display means responsive to the calculation means adapted for displaying the location of said device to an operator.

5. The magnetic resonance tracking system recited in claim 4, wherein the detection means comprises an RF coil affixed to the device for receiving the MR response signal.

6. A method for tracking a location of a device within a subject employing magnetic resonance comprising the steps of:
   a) inserting a device within said subject;
   b) applying a homogeneous magnetic field having substantially uniform amplitude over said subject;
   c) transmitting a zero reference radiofrequency (RF) pulse into said subject sufficient to cause nutation of a selected ensemble of nuclear spins;
   d) detecting a zero reference Magnetic Resonance (MR) response signal from the nutated ensemble of nuclear spins;
   e) calculating a location offset from the zero reference MR response signal;
   f) transmitting a first RF pulse to said subject sufficient to cause nutation of a selected ensemble of nuclear spins;
   g) applying a first readout magnetic field gradient pulse having two oppositely polarized lobes to said subject oriented in a first direction;
   h) detecting a first magnetic resonance (MR) response signal from the selected ensemble of spins through a coil attached to said device;
   i) calculating an approximate location in the first direction from the first MR response signal; and
   j) calculating a location of said device along the first direction by subtracting the location offset from the approximate location in the first direction.

7. The method for tracking a location of a device within a subject as recited in claim 6 further comprising the steps of:
   a) acquiring a medical diagnostic image of said subject; and
   b) superimposing a symbol on the medical diagnostic image at a position representing the calculated location of said device.

8. The method for tracking a location of a device within a subject as recited in claim 7 including the step of time-multiplexing said method with the steps of acquiring a medical diagnostic image.

9. The method for tracking a location of a device within a subject as recited in claim 6, wherein the step of detecting the first MR response signal occurs simultaneously with the step of applying the first readout magnetic field gradient pulse of the magnetic fields in the first direction.

10. The method for tracking a location of a device within a subject as recited in claim 6, wherein the step of calculating an approximate location in the first direction further includes the step of Fourier transforming the MR response signal from time dependency to frequency dependency, and mapping the frequency dependency to an approximate location.

11. The method for tracking a location of a device within a subject as recited in claim 6 wherein the location offset is subtracted from the approximate location in the first direction to allow localization in the first direction.

12. The method for tracking a location of a device within a subject as recited in claim 6 further comprising the steps of:
   a) transmitting a second non-selective RF pulse into said subject;
   b) applying a second readout magnetic field gradient pulse having two oppositely polarized lobes to said subject oriented in a second direction substantially orthogonal to the first direction; and
   c) detecting a second MR response signal concurrently with application to said subject of the second readout magnetic field gradient pulse;
   d) calculating an approximate location in the second direction from the second MR response signal; and
   e) subtracting the location offset from the approximate location in the second direction to allow localization in the first and second directions.

13. The method for tracking a location of a device within a subject as recited in claim 11 further comprising the steps of:
   a) transmitting a third non-selective RF pulse into said subject;
   b) applying a third readout magnetic field gradient pulse having two oppositely polarized lobes to said subject oriented in a third direction substantially orthogonal to the first and second directions;
   c) detecting a third MR response signal concurrently with the application of the third readout magnetic field gradient pulse to said subject;

d) calculating an approximate location in the third direction from the third MR response signal; and e) subtracting the location offset from the approximate location in the third direction to allow localization in the first, second and third directions.

14. The method for tracking a location of a device within a subject employing magnetic resonance comprising the steps of:

a) inserting a device within said subject;

b) applying a homogeneous magnetic field having substantially uniform amplitude over said subject;

c) transmitting a first non-selective radiofrequency (RF) pulse into said subject;

d) applying a first readout magnetic field gradient pulse having two oppositely polarized lobes to said subject oriented in a first direction;

e) detecting a first magnetic resonance (MR) response signal concurrently with step "d" to allow localization in the first direction;

f) computing a first position P1 along the first direction from the first MR response signal;

g) transmitting a second non-selective RF pulse into said subject;

h) applying a second readout magnetic field gradient pulse having two oppositely polarized lobes to said subject oriented in a second direction substantially different from the first direction;

i) detecting a second MR response signal concurrently with step "h" to allow localization in the second direction;

j) computing a second position P2 along the second direction from the second MR response signal;

k) transmitting a third non-selective RF pulse into said subject;

l) applying a third readout magnetic field gradient pulse having two oppositely polarized lobes to said subject oriented in a third direction substantially different from the first and second directions;

m) detecting a third MR response signal concurrently with step "l" to allow localization in the third direction;

n) computing a third position P3 along the third direction from the third MR response signal;

o) transmitting a fourth non-selective RF pulse into said subject;

p) applying a fourth readout magnetic field gradient pulse having two oppositely polarized lobes to said subject oriented in a fourth direction substantially different from the first, second and third directions;

q) detecting a fourth MR response signal concurrently with the application of the fourth readout magnetic field gradient pulse to allow localization in the fourth direction;

r) computing a fourth position P4 along the fourth direction from the fourth MR response signal;

s) computing linear combinations of the positions P1, P2, P3, P4 along the first, second, third and fourth directions to obtain a location of said device that is relatively insensitive to chemical shift differences within said subject.

15. The method for tracking a location of a device within a subject employing magnetic resonance comprising the steps of:

a) inserting a device within said subject;

b) applying a homogeneous magnetic field having substantially uniform amplitude over said subject;

c) transmitting a non-selective radiofrequency (RF) pulse into said subject;

d) concurrently applying three readout magnetic field gradient pulses each having two oppositely polarized lobes oriented along an "X", "Y" and "Z" axis, respectively, to said subject to create a resultant magnetic field gradient oriented in a desired direction;

e) detecting a magnetic resonance (MR) response signal concurrently with step "c" to allow localization in a first direction;

f) transforming the MR response signal;

g) repeating steps "c"-"f" for three additional repetitions each having a readout gradient oriented in a substantially different second, third and fourth direction, respectively, according to a Hadamard encoding method to obtain a first, second, third and fourth transformed MR response signal;

h) computing positions P1, P2, P3, P4 along the first, second, third, and fourth directions from the first, second, third, and fourth MR response signals respectively; and i) computing linear combinations of the positions P1, P2, P3, P4 along the first, second, third and fourth directions according to a Hadamard decoding method to obtain a location of said device that is relatively insensitive to chemical shift differences within said subject.

16. The method for tracking a location of a device within a subject as recited in claim 15 wherein the "X", "Y", "Z" readout gradients are given a selected polarity for the first repetition, the polarity of the "X", "Y" readout gradient is inverted with respect to the readout gradient of the first repetition while the polarity of the "Z" gradients is not inverted for the second repetition, the polarity of the "X", "Z" readout gradient is inverted while the polarity of the "Y" gradients is not inverted for the third repetition, and the polarity of the "Y", "Z" readout gradient is inverted while the polarity of the "X" gradients is not inverted for the fourth repetition.

17. The method for tracking a location of a device within a subject as recited in claim 16 wherein the location of said device is calculated from the linear combinations of the positions P1, P2, P3, P4 along the first, second, third and fourth directions, respectively, according to the following equations:

$$X \text{ position} = -P1 + P2 + P3 - P4$$

$$Y \text{ position} = -P1 + P2 - P3 + P4$$

$$Z \text{ position} = -P1 - P2 + P3 + P4$$

where "X", "Y", "Z" position is the location of said device in three dimensions.

* * * * *